United States Patent
Dams et al.

(10) Patent No.: US 7,998,399 B2
(45) Date of Patent: Aug. 16, 2011

(54) APPARATUS FOR THE DETERMINATION OF A PARAMETER OF A MOLTEN METAL OR A SLAG LAYER LYING ON THE MOLTEN METAL

(75) Inventors: Francis Dams, Kessel-Lo (BE); Guido Jacobus Neyens, Opoeteren (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 867 days.

(21) Appl. No.: 11/626,693

(22) Filed: Jan. 24, 2007

(65) Prior Publication Data

US 2007/0173117 A1    Jul. 26, 2007

(30) Foreign Application Priority Data

Jan. 26, 2006  (DE) .......................... 10 2006 005 476

(51) Int. Cl.
  *C21B 7/24* (2006.01)
  *G01K 1/00* (2006.01)

(52) U.S. Cl. ................ 266/99; 266/78; 266/80; 374/26; 374/139; 374/140

(58) Field of Classification Search ............ 266/78, 266/80, 99; 374/26, 139, 140
  See application file for complete search history.

(56) References Cited

U.S. PATENT DOCUMENTS

| 5,596,134 | A | | 1/1997 | Phillippi et al. | |
| 5,720,553 | A | * | 2/1998 | Falk | ............................ 374/26 |
| 2005/0040570 | A1 | | 2/2005 | Asselborn | |

FOREIGN PATENT DOCUMENTS

| DE | 36 41 225 A1 | 6/1987 |
| DE | 298 05 881 U1 | 8/1998 |
| EP | 0 069 433 B1 | 2/1985 |
| WO | 03/060432 A1 | 7/2003 |
| WO | 03/064714 A1 | 8/2003 |

\* cited by examiner

*Primary Examiner* — Roy King
*Assistant Examiner* — Lois Zheng
(74) *Attorney, Agent, or Firm* — Panitch Schwarze Belisario & Nadel LLP

(57) ABSTRACT

An apparatus is provided for the determination of at least one parameter of a molten metal or a slag layer lying on top of the molten metal. The apparatus has a carrier tube, a measuring head arranged on one end of the carrier tube with a body fixed in the carrier tube. An A/D converter is arranged within the measuring head or the carrier tube, and the A/D converter is connected to at least one sensor arranged in or on the measuring head. The measuring head has a contact piece, which is electrically connected via its contact terminals to the signal output of the A/D converter, and the contact piece is connected to a lance inserted into the carrier tube. No more than two signal lines are arranged within the lance, the signal lines each being connected at one end via a contact terminal of the contact piece to the A/D converter and at an opposite end to a computer or an analysis device.

11 Claims, 6 Drawing Sheets

APPARATUS FOR THE DETERMINATION OF A PARAMETER OF A MOLTEN METAL OR A SLAG LAYER LYING ON THE MOLTEN METAL

BACKGROUND OF THE INVENTION

The invention relates to an apparatus for the determination of at least one parameter of a molten metal (preferably molten iron or steel) or a slag layer lying on top of the molten metal. The apparatus has a carrier tube, on whose one end a measuring head is arranged with a body fixed within the carrier tube. An A/D (analog/digital) converter is arranged within the measuring head or the carrier tube, and the A/D converter is connected to at least one sensor arranged in or on the measuring head.

Apparatuses of this type are known from International application publication No. WO 03/060432 A1. Here, the use of disposable electrical measuring components within a drop-in probe are described, wherein the sensor signals are transmitted wirelessly to an analysis station. The apparatus is therefore not encumbered by a cable during its drop into the molten metal. Conventional immersion probes, that is, probes which are immersed for a short time in the molten metal for measuring or sampling and then withdrawn again, are affixed with their carrier tube on a convention lance (measuring lance), which is known, for example, from German Utility Model DE 298 05 881 U1, European Patent EP 0 069 433 B1, German published patent application DE 36 41 225 A1, or International application publication No. WO 03/064714 A1, through which lance the transmission of the measuring signal occurs.

BRIEF SUMMARY OF THE INVENTION

The underlying objective of the present invention is to make available an improved measuring apparatus, with which an exact measurement of parameters (characteristic properties) of a molten metal or a slag layer lying on top of the molten metal is made possible.

According to the invention, the measuring head has a contact piece, which is electrically connected to a signal output and a power supply line of the A/D converter. Further, the contact piece is connected to a lance inserted into the carrier tube. Within the lance at least one signal line and at least one power supply line are arranged, which are connected at the one end to the contact piece and at the other end to a computer or analytical device, so that a transmission of the measurement signals from the sensors as digital signals is possible. By this means, electrical disturbances caused by the environment are eliminated to a large extent, and a compensation or shielding of the lines is not necessary.

Analog signals are transmitted only over a very short distance, which the power supply enables without problem. In known lance/measurement apparatuses, existing critical points, such as electrical contact terminals and connections, which can generate measurement inaccuracies or false signals, are at least minimized by digital technology and a limitation on the number of lines. Here, all known sensors can in principle be installed, for example temperature sensors, electrochemical sensors, or optical sensors.

The signals are transmitted via a conventional contact piece connected to the lines, which are fed through a lance and which are connected to an analysis device. The lance is a conventional carrier lance, onto which the carrier tube for measurement is pressed and with which the carrier tube is held during the measuring. Here, it is possible to employ the metal sleeve of the lance, or a metal sleeve integrated with or enclosing the measuring head, as one of the two lines. Thus, only one line needs to be fed through the lance. The measuring signals and the power supply can be transmitted via a single line due to the use of digital technology.

The contact piece is preferably electrically connected to a power supply connection of the A/D converter. Advantageously, there are at most two signal lines arranged within the lance for transmission of digital signals, which lines are each connected at the one end to a contact terminal of the contact piece and at the other end to a computer or analysis device.

It is preferred to have a power supply line arranged within the lance, which is connected at the one end to a contact terminal of the contact piece and at the other end to a power source.

Within the lance a signal line can be arranged, connected at the one end to a contact terminal of the contact piece and at the other end to a measuring or analysis device. A second signal line can be formed using the metal tube of the lance, which is electrically connected to one contact terminal of the contact piece. A signal line arranged within the lance can also function as the power supply line and be connected to a power source.

The apparatus according to the invention can be embodied as a so-called drop-in probe, that is, a probe dropped from a repository at a certain height into the molten metal. The apparatus has no lance in this embodiment, but can be equipped with a carrier tube. This embodiment of the apparatus for the determination of at least one parameter of a molten metal or a slag layer lying on top of the molten metal, having a measuring head with an A/D converter arranged within the measuring head and connected to at least one sensor arranged on or in the measuring head, is characterized by a signal output of the A/D converter being connected to at most two signal lines, which are connected to a computer or an analysis device.

It is advantageous that a contact piece be arranged between the A/D converter and the computer or the analysis device, preferably between the signal line and the computer or the analysis device. Via the contact piece the A/D converter is electrically connected to the computer or the analysis device. Preferably, the contact piece is electrically connected to a power supply connection of the A/D converter.

The A/D converter can be arranged on a printed circuit board or on a circuit frame or another device designed to accommodate electrical components.

The invention further relates to an embodiment of a measuring apparatus comprising a previously described apparatus and a molten metal arranged in a melt container, in which the apparatus is at least partially immersed. In this embodiment the A/D converter is connected to the bath contact of the apparatus, and the molten metal forms one part of the electrical connection between the bath contact and a computer or an analysis device.

In the apparatus embodiments according to the invention, all of the electronic measuring components are in principle constructed as single-use material, which are disposed of, along with the measuring head and the carrier tube, after a single use. The measuring head can carry additional sensors, for example oxygen sensors, optical sensors, or temperature sensors, which can be connected to an electronic analysis device in a conventional manner via the contact piece. The shunting of the ground potential can occur not only via a signal line, but instead via the molten metal, so that, in principle, only one signal line in the form of a cable is sufficient.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
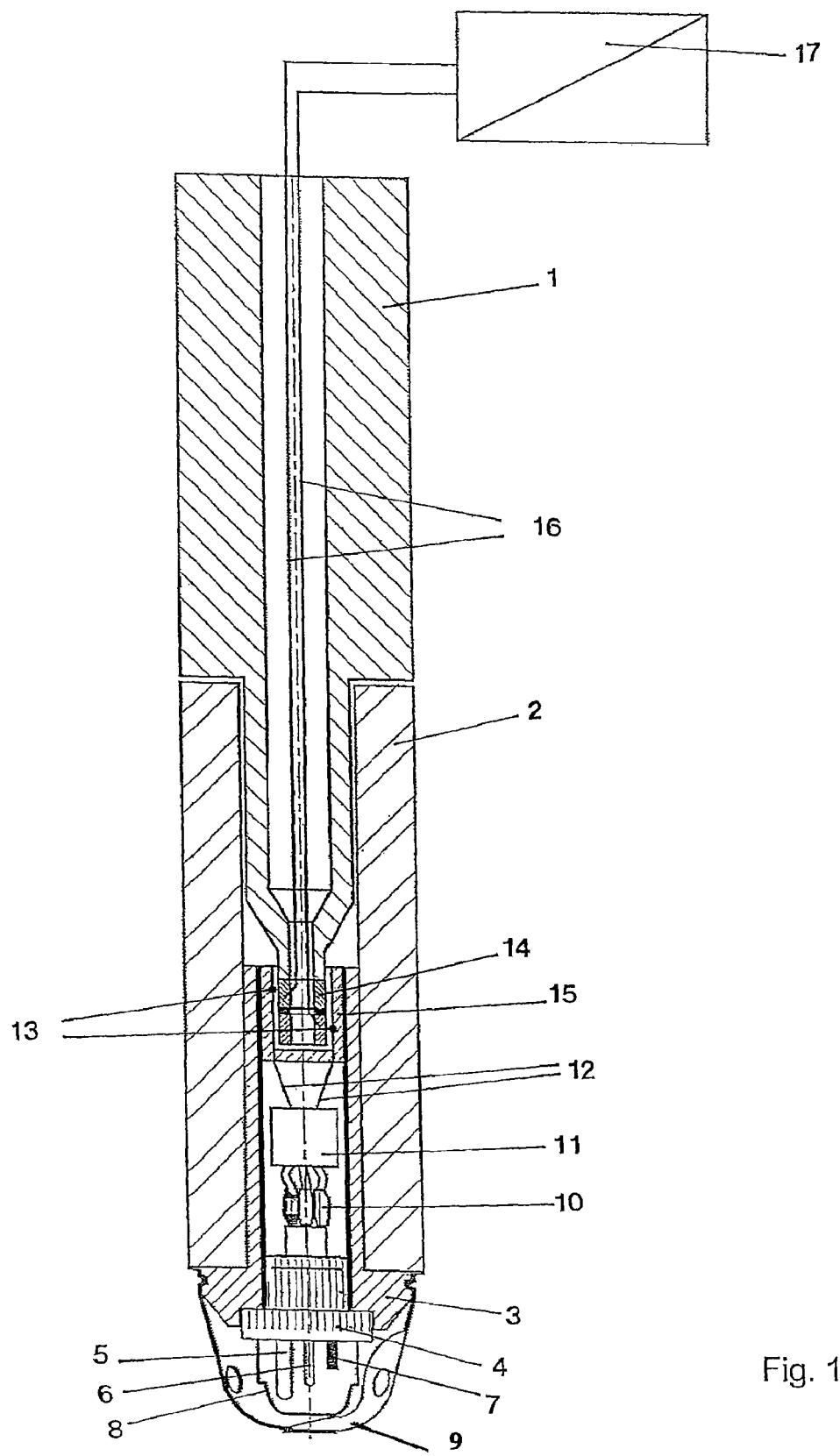
FIG. 1 is a schematic diagram and a longitudinal sectional view of a sublance according to one embodiment of the invention.

The apparatus according to the invention represented in FIG. 1 concerns a so-called sublance. A carrier tube 2 with a measuring head 3 is arranged on a lance 1. The carrier tube 2 is formed of cardboard, and the measuring head 3 is formed essentially of a refractory material, such as cement or foundry sand. The measuring head 3 has a sensor carrier 4, on whose outer end (the immersion end) an oxygen sensor 5, a temperature sensor 6, and the so-called bath contact 7 are arranged. The sensors are protected up to the beginning of the measurement by a first protective cap 8, which is affixed to the sensor carrier 4. The entire portion of the measuring head 3 protruding out of the carrier tube 2, is enclosed in an additional protective cap 9.

On the rear end of the sensor carrier 4, arranged within the measuring head 3, a so-called wire connection 10 is arranged, which connects the sensors 5; 6; 7 to an A/D converter 11. The A/D converter 11 has two signal lines 12 on its other end (output side), which are connected to corresponding contact terminals 13 of a contact piece 15. The contact piece 15 is arranged on a mechanical connector 14 (which serves as the mechanical connection of the lance 1 to the measuring head 3). On the rear end of the contact piece 15 two signal lines 16 are arranged, which are connected through the lance 1 to a power source and/or an analysis device 17.

Figure 2:
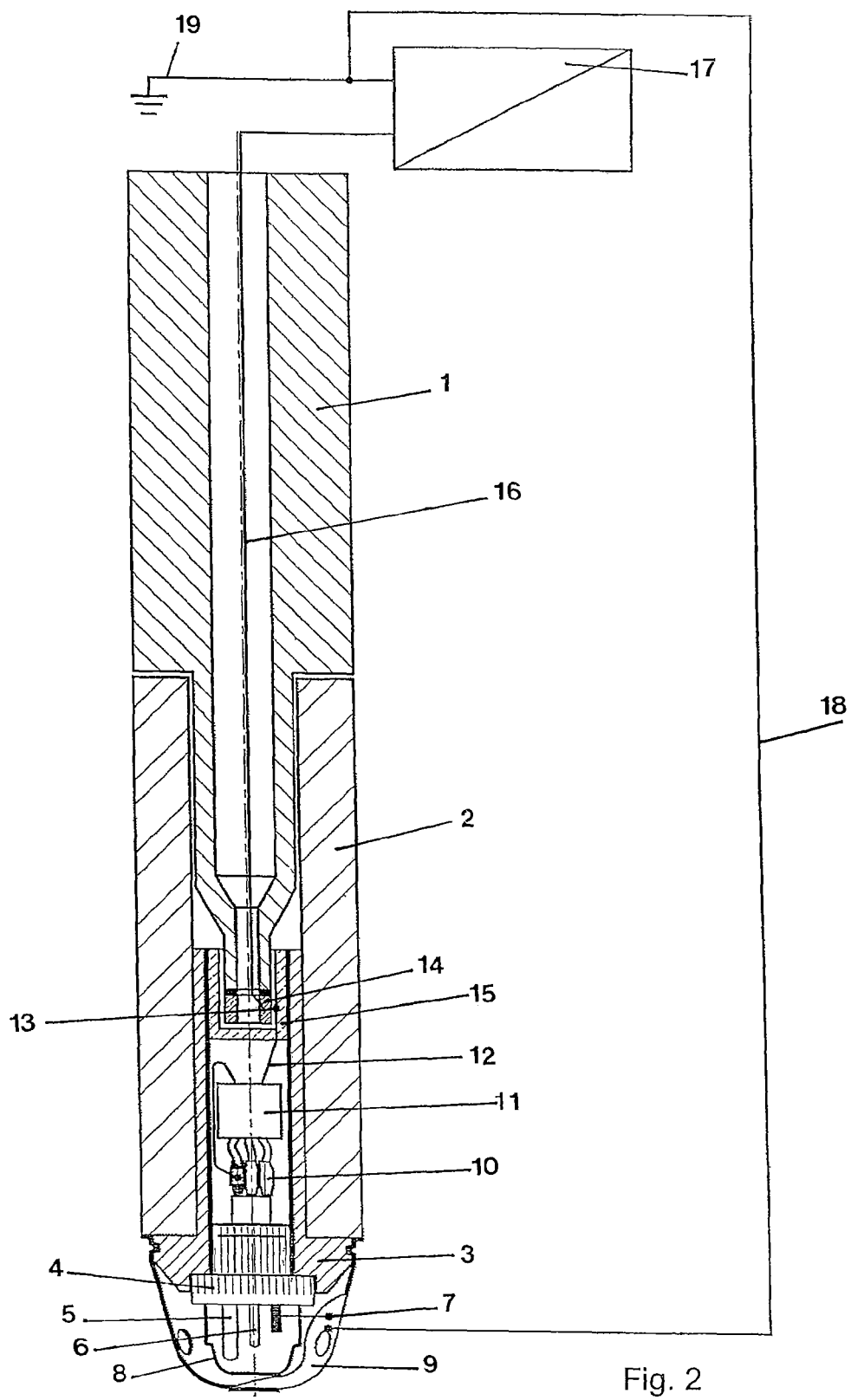
FIG. 2 is a schematic diagram and a longitudinal sectional view similar to FIG. 1 of a sublance according to another embodiment of the invention.

The sublance represented in FIG. 2 is constructed similarly to the sublance represented in FIG. 1. They differ in that the A/D converter 11 is only connected via one signal line 12 to the contact piece 15 and only one signal line 16 is fed through the carrier tube 1 from the contact piece 15 to the analysis device 17 and/or to a power source. The second line required to form an electrical circuit is formed by the bath contact which, after the immersion in the molten metal, is applied to the ground potential 19 via the molten metal by means of the signal line 18 (corresponding to the molten metal) symbolically represented in FIG. 2. The ground potential 19 is connected to the analysis device 17.

Figure 3:
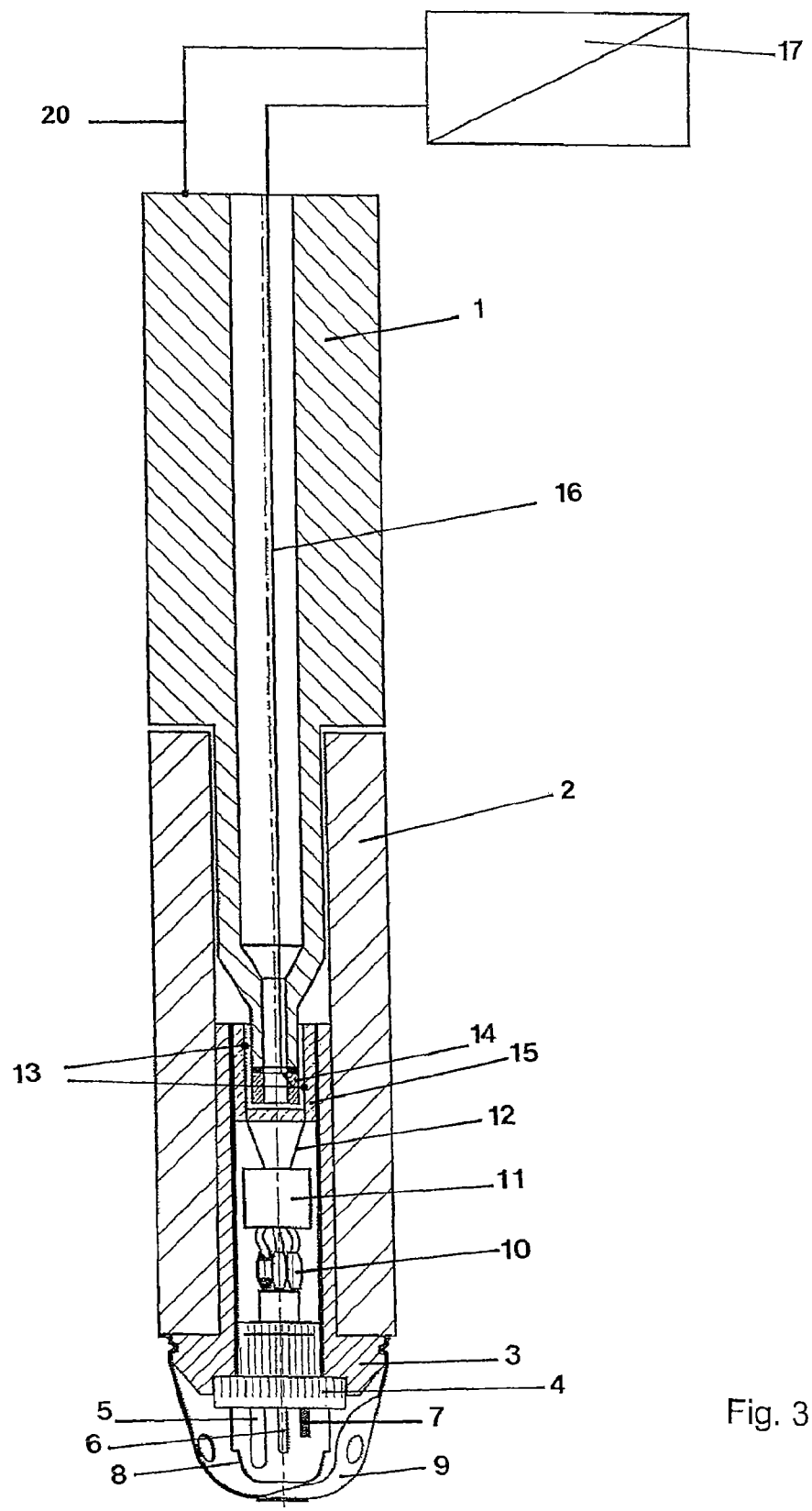
FIG. 3 is a schematic diagram and a longitudinal sectional view similar to FIG. 1 of a sublance according to a further embodiment of the invention.

The sublance represented in FIG. 3 is likewise constructed similarly to FIG. 1. Unlike FIG. 1, the contact piece 14 is electrically connected at its end facing away from the A/D converter 11 to a signal line 16, which is fed through the lance 1, as well as to the lance 1 itself. The lance 1 is constructed at least partially of metal, is thus conductive, and is connected at its non-immersion end to the analysis device 17 via a ground line 20.

Figure 4:
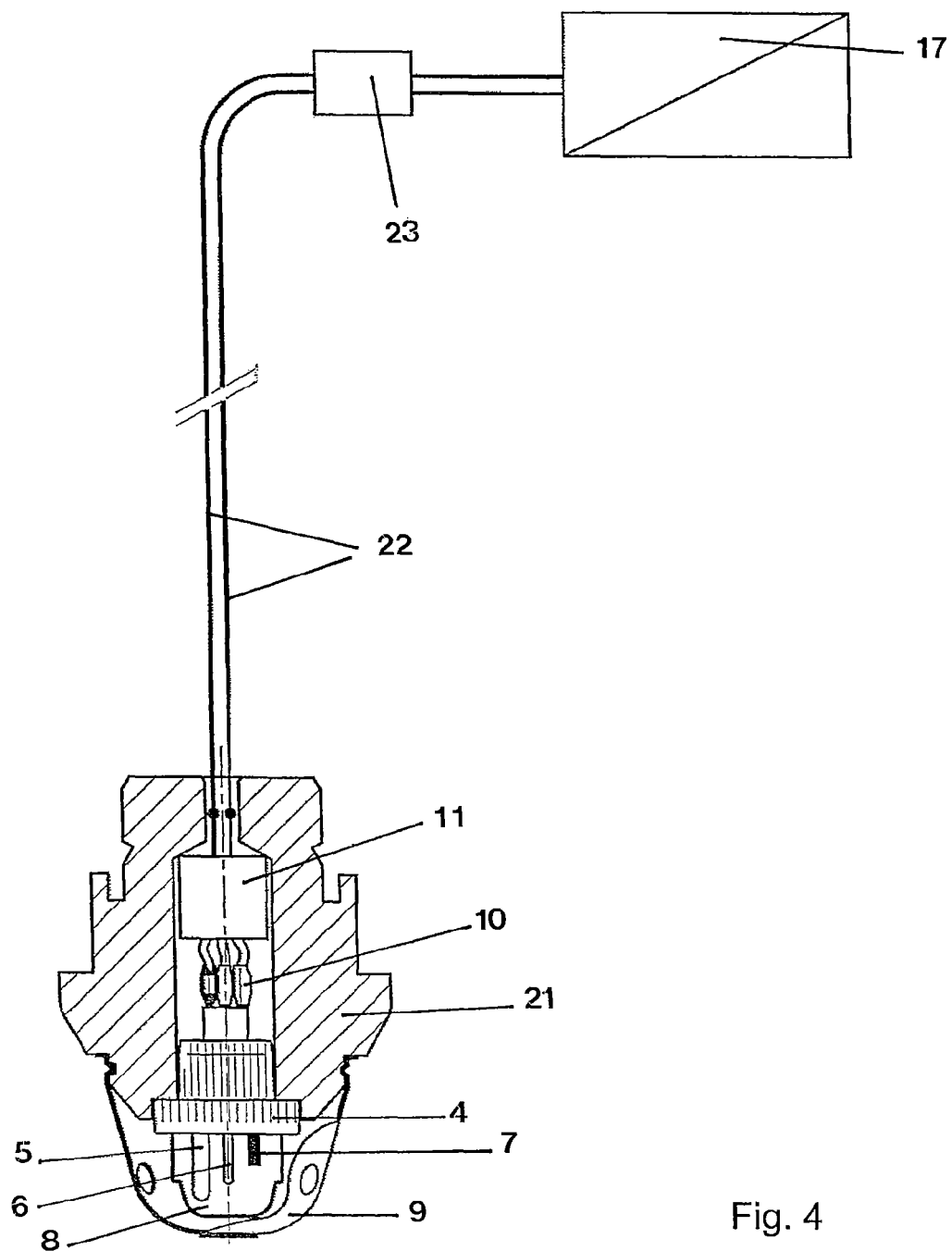
FIG. 4 is a schematic diagram and a longitudinal sectional view of a drop-in probe according to the invention.

An embodiment of the invention as a so-called drop-in sensor 21 is represented in FIG. 4. The drop-in sensor 21 is dropped from a greater height, usually automatically, into the molted metal. The drop-in sensor 21 is connected via the signal cable 22 to a contact piece 23, which is usually arranged in proximity to the drop point and is connected to the analysis device 17 and/or the power source. The internal construction of the drop-in sensor 21 with the sensors corresponds essentially to the construction of the measuring head according to FIG. 1.

Figure 5:
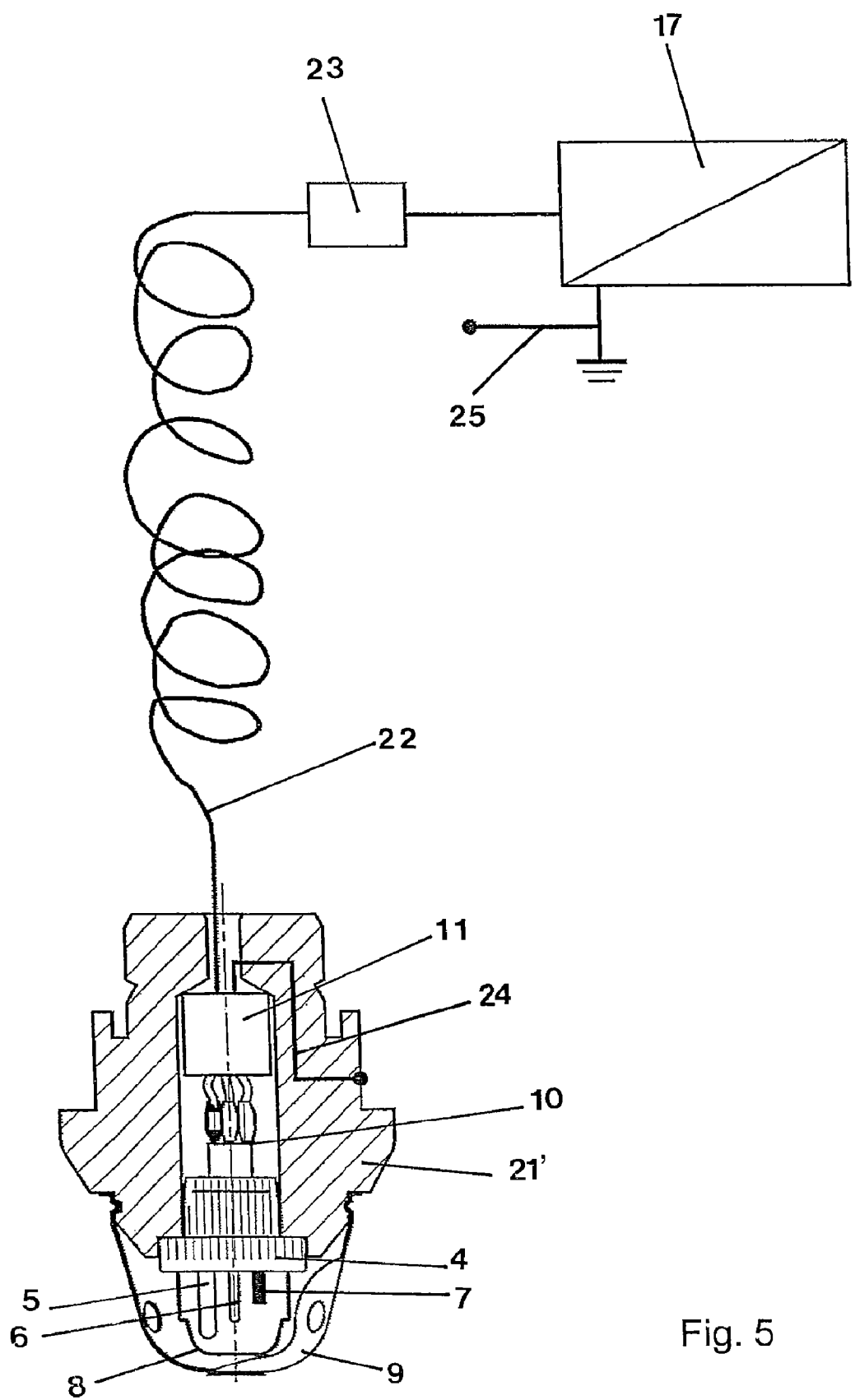
FIG. 5 is a schematic diagram and a longitudinal sectional view similar to FIG. 4 of a second embodiment of a drop-in probe according to the invention.
Figure 6:
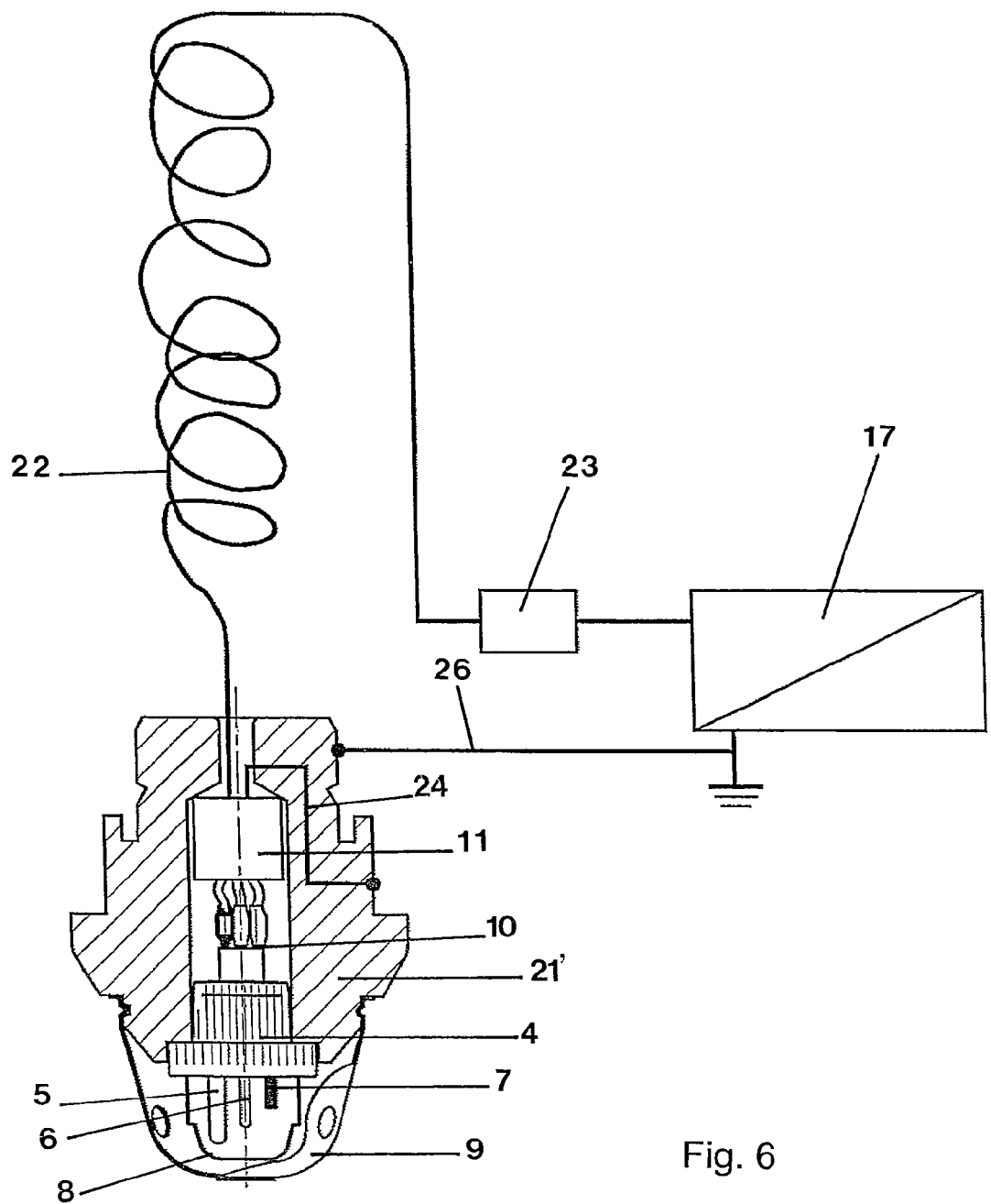
FIG. 6 is a schematic diagram of the drop-in probe according to FIG. 5, during the measurement in the melt.

The drop-in sensor 21' represented in FIG. 5 is similarly constructed. It has, however, only one signal line 22 leading away from the A/D converter. The second line (the ground line) is realized via the molten metal, similarly to the arrangement in FIG. 2, following the immersion of the drop-in sensor 21' into the molten metal (FIG. 6). For this purpose, within the drop-in sensor 21', the A/D converter is connected, at its end opposite from the sensor carrier (opposite in the sense of electrical connection), to a ground contact 24 as well as to the signal line 22.

The ground contact 24 is connected via the material of the drop-in sensor 21' through the molten metal. The molten metal lies at the ground potential, so that it is connected to the analysis device 17 via the ground line 25 of the analysis device. This type of contacting is therefore similar to the circuit represented in FIG. 2. In FIG. 6 the drop-in sensor 21' is represented during the measurement in the steel melt (the molten metal is not shown in the drawing). The ground line through the steel melt is designated by the reference numeral 26. This ground line connects the drop-in sensor 21' to the analysis device 17.

The body of the drop-in sensors 21; 21' is made of steel, in order to guarantee penetration of the slag lying on top of the molten metal (for example a steel melt) and to make possible the contacting according to FIGS. 5 and 6.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An apparatus for determination of at least one parameter of a molten metal or a slag layer lying on top of the molten metal, comprising:
    a carrier tube,
    a measuring head arranged on one end of the carrier tube and having a body affixed in the carrier tube,
    a contact piece which is electrically connected via its contact terminals to a signal output of the A/D converter, the contact piece providing for a lance to be inserted into the carrier tube, and
    an A/D converter arranged within the measuring head or the carrier tube, the A/D converter being connected to at least one sensor arranged on or in the measuring head,
    wherein within the lance a first A/D signal carrying line is conductively connected at one end to an output of the A/D converter via a contact terminal of the contact piece and at an opposite end is conductively connectable to a computer or an analysis device, and wherein a second conductive A/D signal carrying line is formed between the output of the A/D converter and the computer or the analysis device by one of the molten metal, the slag layer and a metal sleeve of the lance via the contact piece.

2. The apparatus according to claim 1, wherein the contact piece is electrically connected to a power supply connection of the A/D converter.

3. The apparatus according to claim 1, wherein at least one of the signal lines is for the transmission of digital signals.

4. The apparatus according to claim 1, wherein the one of the signal lines functioning as a power supply line, is connected at one end to a contact terminal of the contact piece and at an opposite end conductively connectable to a power source.

5. The apparatus according to claim 1, wherein the one of the A/D signal carrying lines arranged within the lance also functions as a power supply line and is connectable to an external power source.

6. The apparatus according to claim 1, wherein the A/D converter is arranged on a printed circuit board.

7. A measuring system comprising an apparatus according to claim 1 and a molten metal arranged within a melt container, the apparatus being at least partially immersed in the molten metal, wherein the A/D converter is connected to a bath contact of the apparatus to form the second A/D signal carrying line.

8. An apparatus for determination of at least one parameter of a molten metal or a slag layer lying on top of the molten metal, comprising:
   a measuring head, and
   an A/D converter arranged within the measuring head, the A/D converter being connected to at least one sensor arranged on or in the measuring head,
   wherein a signal output of the A/D converter is conductively connectable to a computer or an analysis device by no more than two signal carrying lines, and
   wherein a first one of the A/D signal carrying lines, is arranged within a lance, and a second one of the A/D signal carrying lines is formed by one of the molten metal, the slag layer and a metal sleeve of the lance.

9. The apparatus according to claim 8, wherein a contact piece is arranged between the A/D converter and the computer or the analysis device, through which contact piece, the A/D converter is conductively connected to the computer or the analysis device.

10. The apparatus according to claim 9, wherein the contact piece is arranged between the signal lines and the computer or the analysis device, and between the signal lines and a power source.

11. The apparatus according to claim 9, wherein the contact piece is electrically connectable to a power supply connection of the A/D converter.

* * * * *